US012806143B2

(12) United States Patent
Cui et al.

(10) Patent No.: US 12,806,143 B2
(45) Date of Patent: Nov. 24, 2026

(54) HIGH-EFFICIENCY AND LOW-TOXICITY DNA AND RNA LIPID DELIVERY CARRIER

(71) Applicant: REVIVO THERAPEUTICS CO., LTD., Hangzhou (CN)

(72) Inventors: Yanfang Cui, Wuhan (CN); Shuaijie Ji, Wuhan (CN); Baoqian Zhang, Wuhan (CN)

(73) Assignee: REVIVO THERAPEUTICS CO., LTD., Hangzhou (CN)

( * ) Notice: Subject to any disclaimer, the term of this patent is extended or adjusted under 35 U.S.C. 154(b) by 144 days.

(21) Appl. No.: 18/721,013

(22) PCT Filed: Dec. 15, 2022

(86) PCT No.: PCT/CN2022/139186
§ 371 (c)(1),
(2) Date: Jun. 17, 2024

(87) PCT Pub. No.: WO2023/109881
PCT Pub. Date: Jun. 22, 2023

(65) Prior Publication Data

US 2025/0049712 A1 Feb. 13, 2025

(30) Foreign Application Priority Data

Dec. 15, 2021 (CN) ......................... 202111533616.1

(51) Int. Cl.
*A61K 31/7105* (2006.01)
*A61K 9/00* (2006.01)
(Continued)

(52) U.S. Cl.
CPC .......... *A61K 9/1271* (2013.01); *A61K 9/0019* (2013.01); *A61K 9/5123* (2013.01); (Continued)

(58) Field of Classification Search
None
See application file for complete search history.

(56) References Cited

FOREIGN PATENT DOCUMENTS

CN 103380113 A 10/2013
CN 106661138 A 5/2017
(Continued)

OTHER PUBLICATIONS

Twyman, Lance J., et al., "An Approach for the Rapid Synthesis of Moderately Sized Dendritic Macromolecules", Article, The Chemical Laboratory, The University of Kent, Canterbury, Kent CT2 7NH, UK, vol. 23, Issue 4, 5 pages (1994).

*Primary Examiner* — Ernst V Arnold
(74) *Attorney, Agent, or Firm* — Dinsmore & Shohl LLP

(57) ABSTRACT

Provided in the present invention is a high-efficiency and low-toxicity DNA and RNA lipid delivery carrier. In order to enrich the types of nucleic acid drug delivery carriers, improve the in-vivo delivery and expression effects of the nucleic acid drug and reduce the toxicity and side effects, a new ionizable lipid compound having a special structure is provided in the present invention. The compound has a good binding effect with a negatively-charged nucleic acid, which effectively prevents the premature degradation of the nucleic acid by a nuclease in a cell and facilitates the passage of a liposome loaded with the nucleic acid through a cell membrane. Effective degradation and rapid removal can be achieved, the toxicity and side effects of the nucleic acid drug are reduced, and a nucleic acid drug delivery carrier truly having a high transfection efficiency, a high expression level and a low toxicity can be formed.

20 Claims, 13 Drawing Sheets

(51) Int. Cl.

| | |
|---|---|
| ***A61K 9/1271*** | (2025.01) |
| ***A61K 9/51*** | (2006.01) |
| ***B82Y 5/00*** | (2011.01) |
| ***C07C 229/16*** | (2006.01) |

(52) U.S. Cl.
CPC ........ *A61K 31/7105* (2013.01); *C07C 229/16* (2013.01); *B82Y 5/00* (2013.01)

(56) References Cited

FOREIGN PATENT DOCUMENTS

| | | | | | |
|---|---|---|---|---|---|
| CN | 113402404 | A | | 9/2021 | |
| CN | 114163345 | A | | 3/2022 | |
| CN | 114191561 | A | * | 3/2022 | ............. A61K 47/18 |
| CN | 114262275 | A | | 4/2022 | |
| WO | 2006006196 | A2 | | 1/2006 | |
| WO | 2012068176 | A1 | | 5/2012 | |
| WO | 2017118842 | A1 | | 7/2017 | |
| WO | 2021156469 | A1 | | 8/2021 | |

* cited by examiner

Chemical Formula: $C_{78}H_{145}N_3O_9$

Molecular Weight: 1269.03

HIGH-EFFICIENCY AND LOW-TOXICITY DNA AND RNA LIPID DELIVERY CARRIER

CROSS-REFERENCE TO RELATED APPLICATIONS

This application is a national-stage entry under 35 U.S.C. § 371 of International Application PCT/CN2022/139186, filed Dec. 15, 2022, which International Application claims the benefit of priority to Chinese Patent Application No. 202111533616.1, filed Dec. 15, 2021.

TECHNICAL FIELD

The present disclosure belongs to the field of nucleic acid drug delivery carriers, and in particular, relates to a high-efficiency and low-toxicity DNA and RNA lipid delivery carrier.

BACKGROUND

Currently, lipid delivery carriers have been widely used in drug delivery, especially with the development of nucleic acid drugs, the application of lipid delivery carriers has been advancing rapidly. Due to their negative charge, nucleic acid molecules are not conducive to cell membrane interaction, resulting in poor cell permeability, and the nucleic acids in the exposed state that enter tissues or cells are easily degraded by nucleases, nucleic acid transfection not only requires the successful transport of nucleic acids with biological functions into cells, but also needs to ensure that nucleic acids can maintain their biological functions in cells. The commonly used vectors in research and clinical application comprise viral vectors and non-viral vectors, liposome carriers belong to non-viral vectors, which have higher nucleic acid transfection efficiency, lower cytotoxicity, more convenient preparation process and higher practicability than viral vectors, so they have attracted more and more attention.

With the deepening of research, relevant researchers have actively developed a variety of liposome carriers to continuously improve the safety and efficiency. The process of the most common carriers formed by cationic lipid compounds in the early stage is: liposome-nucleic acid drug complexes are formed by positively charged cationic lipid compounds and negatively charged nucleic acids, the cationic liposome-nucleic acid drug complexes have an overall positively charged surface, and are adsorbed to negatively charged cell surfaces through electrostatic interaction, and enter cells through endocytosis to form endosomes. The cationic lipids in cationic liposomes interact electrostatically with the negatively charged lipids in endosomes, the negatively charged lipids flip from the outside of the endosomes to the inside to form neutral ion pairs with the positively charged lipids, and nucleic acid drugs detach from the cationic lipids. In 2018, FDA approved the first siRNA drug (patisiran [onpattro]), and the delivery carrier used for this nucleic acid drug was Dlin-MC3-DMA liposomes. Recently, ionizable lipids have attracted much attention due to their ability to change their electrical properties in response to pH in the environment.

Although ionizable lipids have made the latest progress in drug delivery, showing advantages over viral vectors and other types of non-viral vectors in terms of encapsulation efficiency, nucleic acid expression, cytotoxicity, etc., there are still very few ionizable lipid molecules available for use, and most of them are prone to distribution in liver organs and increase the metabolic burden on the liver, resulting in toxicity and side effects and other issues. Therefore, it is still necessary to explore more ionizable lipid compounds suitable for nucleic acid drug applications, and develop nucleic acid drug delivery carriers that truly take into account high transfection efficiency, high expression effect and low toxicity.

SUMMARY

The purpose of the present disclosure is to provide an ionizable lipid compound with simple preparation method, combination with nucleic acid and degradation, which enriches the types of ionizable lipid compounds and provides more options for nucleic acid drug delivery.

Another object of the present disclosure is to provide a delivery carrier, which is a high-efficiency and low toxicity lipid delivery carrier for delivering DNA and RNA. The delivery carrier and a nucleic acid molecule encapsulated in the delivery carrier form a pharmaceutical composition, ensuring the activity of the nucleic acid drug and high expression efficiency of the nucleic acid molecule, while reducing the distribution of the drug in the liver.

To solve the above technical problems, the present disclosure employs the following technical solution:

An ionizable lipid compound shown in general formula (I) or general formula (II),

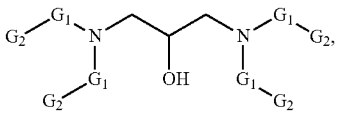

(I)

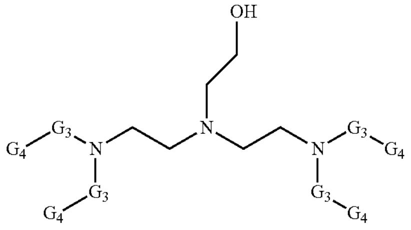

(II)

wherein, in general formula (I), $G_1$ is $C_1$-$C_{10}$ linear alkylidene, $G_2$ is —OC(=O)R, —C(=O)OR or —C(=O)NHR, R is $C_5$-$C_{20}$ linear alkyl or

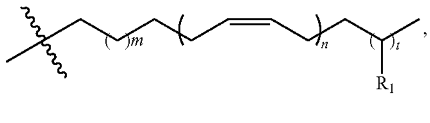

, $R_1$ is hydrogen, methyl, ethyl, or isopropyl, m is an integer between 1~10, n is an integer between 1~5, and f is an integer between 1~5;

in general formula (II), $G_3$ is $C_1$-$C_{10}$ linear alkylidene, $G_4$ is —OC(=O)R', —C(=O)OR' or —C(=O)NHR', R' is

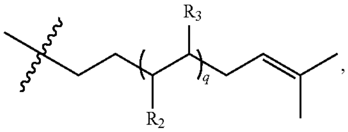

$R_2$ and $R_3$ are independently hydrogen, methyl, ethyl, or isopropyl, q is an integer between 1~3.

Optionally, $G_1$ is $C_2$-$C_8$ linear alkylidene.

Optionally, $G_3$ is $C_5$-$C_{10}$ linear alkylidene.

Optionally, $R_1$ is hydrogen.

Optionally, m is an integer between 3~8, further optionally an integer between 4~6.

Optionally, f is an integer between 1~4, optionally 2 or 3.

Optionally, R is $C_5$-$C_{15}$ linear alkyl or

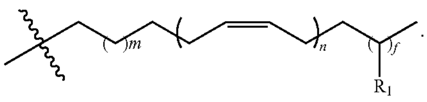

Optionally, $G_2$ is —C(=O)OR.

Optionally, $G_4$ is —C(=O)OR'.

Optionally, one of $R_2$ and $R_3$ is hydrogen, and the other one is methyl, ethyl, or isopropyl.

Further optionally, one of $R_2$ and $R_3$ is hydrogen, and the other one is methyl.

Optionally, $R_2$ is methyl, and $R_3$ is hydrogen.

According to some specific implementations, the ionizable lipid compound is one or more of the following compounds:

The present disclosure also provides a delivery carrier, which comprises one or more of the ionizable lipid compounds shown in general formula (I) and general formula (II).

Optionally, the delivery carrier further comprises a helper molecule.

Optionally, the feeding molar ratio of the ionizable lipid compound to the helper molecule is (0.1~1):(0.1~1), and optionally (0.5~1):(0.5~1).

The helper molecule may be commonly used helper molecules in the art.

Optionally, the helper molecule comprises one or more of synthetic or naturally sourced helper lipid or lipoid molecules, animal sources of any species and any type of cells or vesicles (including exosomes) or their components, polypeptide molecules, polymer molecules, carbohydrate molecules or inorganic substances.

Optionally, the helper molecule comprises one or more of cholesterol, calcipotriol, stigmasterol, β-sitosterol, lupeol, betulin, ursolic acid, oleanolic acid, dioleoyl phosphatidylcholine, distearoyl phosphatidylcholine, 1-stearoyl-2-oleoyl phosphatidylcholine, dioleoyl phosphatidylethanolamine, (1,2-dioleyloxy-propyl) trimethylammonium chloride, didecyl dimethyl ammonium bromide, 1,2-dimyristoyl-sn-glycero-3-ethyl phosphocholine, dipalmitoyl phosphatidylethanolamine-methoxy polyethylene glycol 5000, distearoyl phosphatidylethanolamine-polyethylene glycol 2000, activated carbon, silica and calcium phosphate.

Optionally, the ionizable lipid compound and/or the helper molecule is modified with a targeting substance.

Optionally, the targeting substance comprises one or more of folic acid, single-chain antibodies and targeting polypeptides.

Optionally, the delivery carrier is a lipid nanoparticle.

Optionally, the average size of the nanoparticle preparation is 50 nm~200 nm.

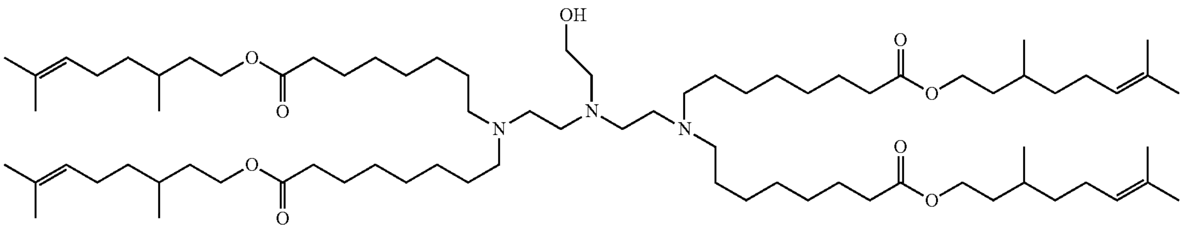

,

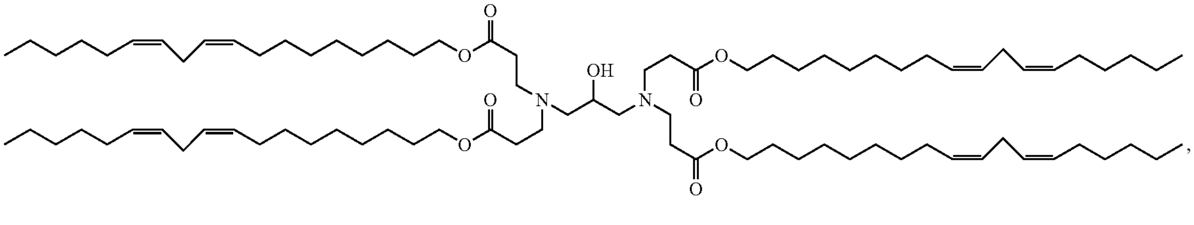

,

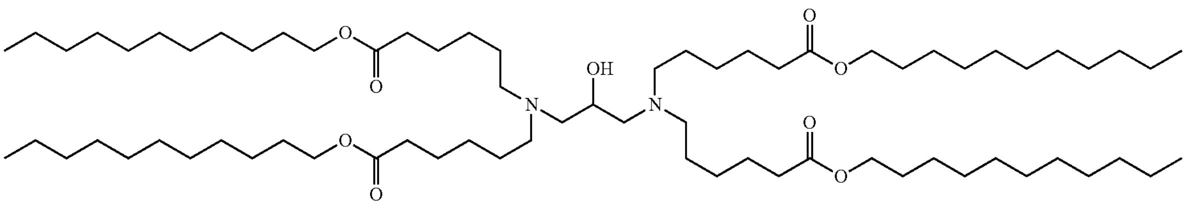

.

Optionally, the average size of the nanoparticle preparation is 50 nm~150 nm.

Optionally, the polydispersity index of the nanoparticle preparation is ≤0.4.

More further, the polydispersity index of the nanoparticle preparation is ≤0.3.

The delivery carrier described in the present disclosure and a nucleic acid molecule encapsulated in the delivery carrier together form a nucleic acid drug composition.

Optionally, the nucleic acid molecule is one or more of pDNA, siRNA, ASO, and mRNA.

Optionally, the mass ratio of the nucleic acid molecule to the delivery carrier is 1:(5~50), optionally 1:(5~40), optionally 1:(5~30).

Optionally, the nucleic acid drug composition comprises a pharmaceutical available additive, and the additive comprises one or more of an excipient, a stabilizer, and a diluent.

Further, the additive comprises, but is not limited to, sucrose, trehalose or other stabilizers.

Optionally, the amount of the additive accounts for 1%~20% of the total mass of the drug composition.

Optionally, the nucleic acid drug composition may be a freeze-dried powder or an injection, the injection is locally administered by microneedles, injection or perfusion through muscle, subcutaneous, endothelium or intra-tumor, or is administered by intravenous injection.

In the present disclosure, the delivery carrier or the nucleic acid drug composition is used for delivering nucleic acid molecules to mammalian cells.

Optionally, the mammal is human.

The present disclosure further provides a method for in vivo delivery of nucleic acid molecules, which uses the delivery carrier to deliver the nucleic acid molecules to the body of a subject.

Optionally, the subject is a mammal.

Optionally, the subject is human.

The present disclosure has the following advantages over the prior art:

The present disclosure provides a new ionizable lipid compound, and enriches the types of ionizable lipid compounds, a delivery carrier formed thereby has the advantages of high encapsulation efficiency and low toxicity, and can efficiently deliver and express nucleic acid drugs in vivo, thus providing more options for nucleic acid drug delivery, which is advantageous for the development and application of nucleic acid drugs.

BRIEF DESCRIPTION OF THE DRAWINGS

FIG. 1 shows a hydrogen spectrum of Compound a;

DETAILED DESCRIPTION

Figure 1:
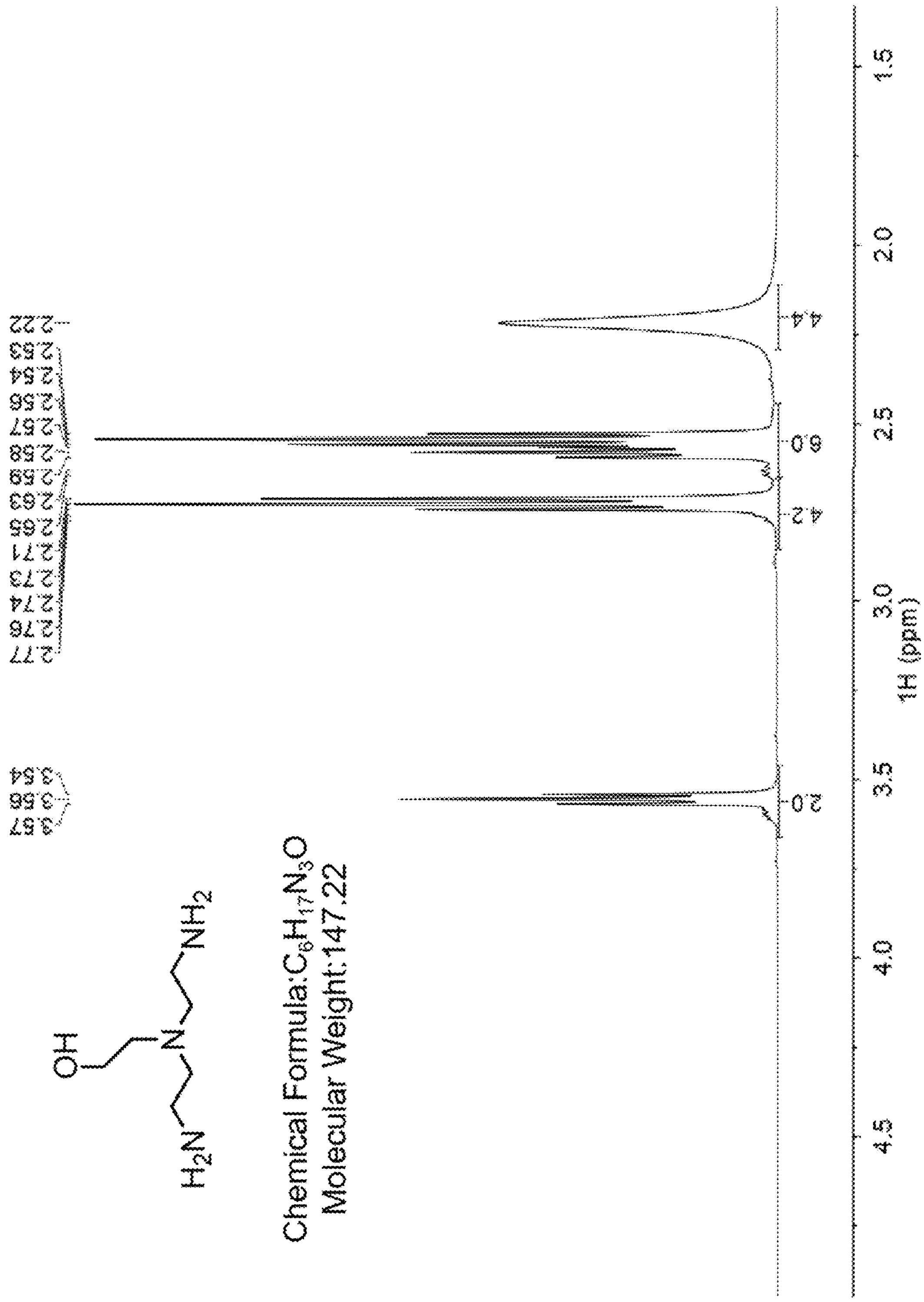

The present disclosure is further described below in combination with the working Examples. However, the present disclosure is not limited to the following Examples. The implementation conditions used in the examples may be further adjusted according to different requirements of specific use, and undefined implementation conditions usually are conventional conditions in the industry. The technical features involved in the various implementations of the present disclosure may be combined with each other as long as they do not conflict with each other.

In order to reduce the toxicity and side effects caused by the accumulated expression of drug components in liver organs, reduce the production cost of nucleic acid drug delivery carriers, and improve the in vivo delivery and expression effects of nucleic acid drugs, the inventors have carried out a lot of research and experimental verification, and developed a new ionizable lipid compound, which can truly form a nucleic acid drug delivery carrier with high transfection efficiency, high expression effect and low toxicity.

In the present disclosure, the ionizable lipid compound is a compound shown in general formula (I) or general formula (II), (I)

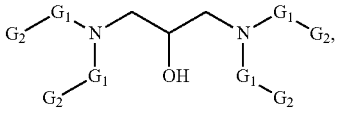

(II)

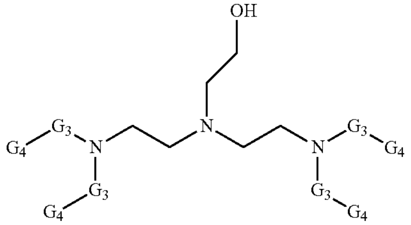

wherein, in general formula (I), $G_1$ is $C_1$-$C_{10}$ linear alkylidene, $G_2$ is —OC(=O)R, —C(=O)OR or —C(=O)NHR, R is $C_5$-$C_{20}$ linear alkyl or

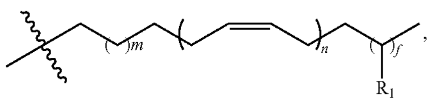

$R_1$ is hydrogen, methyl, ethyl, or isopropyl, m is an integer between 1~10, n is an integer between 1~5, and f is an integer between 1~5;

in general formula (II), $G_3$ is $C_1$-$C_{10}$ linear alkylidene, $G_4$ is —OC(═O)R', —C(═O)OR' or —C(═O)NHR', R' is

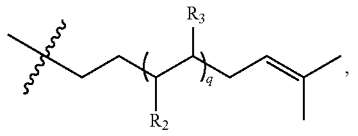

$R_2$ and $R_3$ are independently hydrogen, methyl, ethyl, or isopropyl, q is an integer between 1~3.

Through the structure of the ionizable lipid compound, its binding ability with negatively charged nucleic acids may be improved, the premature degradation of nucleic acids by nucleases in cells may be prevented, and it is beneficial for lipid nanoparticles loaded with nucleic acids to cross cell membranes, effective degradation and rapid in vivo clearance may be achieved, and the toxicity and side effects of nucleic acid drugs are reduced.

According to the present disclosure, the delivery carrier comprises one or more of the ionizable lipid compounds shown in general formula (I) and general formula (II), and selectively a helper molecule.

According to the present disclosure, the delivery carrier is a lipid nanoparticle with a particle size of 50 nm~200 nm.

According to the present disclosure, the nucleic acid molecule may be used for the delivery of one or more of pDNA, siRNA, ASO, and mRNA.

According to the present disclosure, the delivery carrier and a nucleic acid molecule encapsulated in the delivery carrier together form a nucleic acid drug composition, and the nucleic acid is one or more of pDNA, siRNA, ASO, and mRNA.

According to the present disclosure, the nucleic acid drug composition may be a freeze-dried powder or an injection, the injection is locally administered by microneedles, injection or perfusion through muscle, subcutaneous, endothelium or intra-tumor, or is administered by intravenous injection.

In the present disclosure, the delivery carrier or the nucleic acid drug composition is used for delivering nucleic acid molecules to mammalian cells, the mammal is optionally human.

The technical solution and technical effects of the present disclosure is further described below combining with specific embodiments.

In the following Examples, unless otherwise specified, they are all conventional methods; the experimental materials used, unless otherwise specified, were purchased from conventional biochemical reagent manufacturers.

Example 1

The synthesis route of Compound 1:

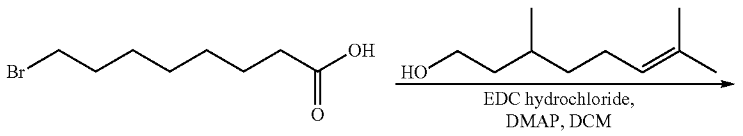

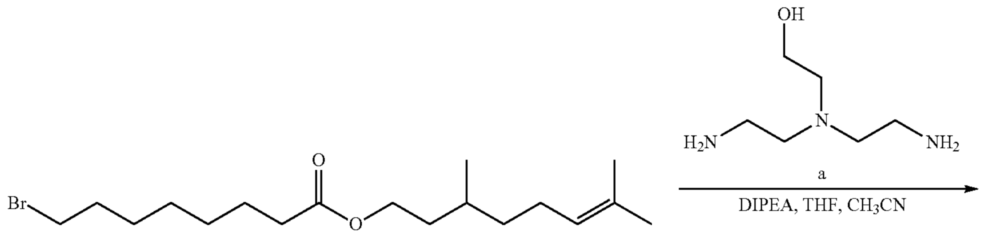

1-1

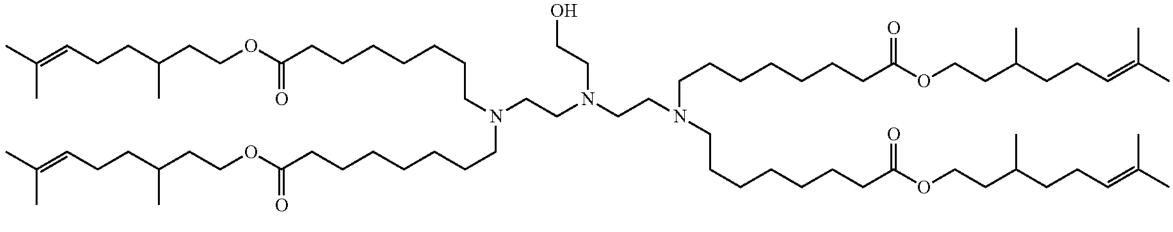

1

Figure 3:
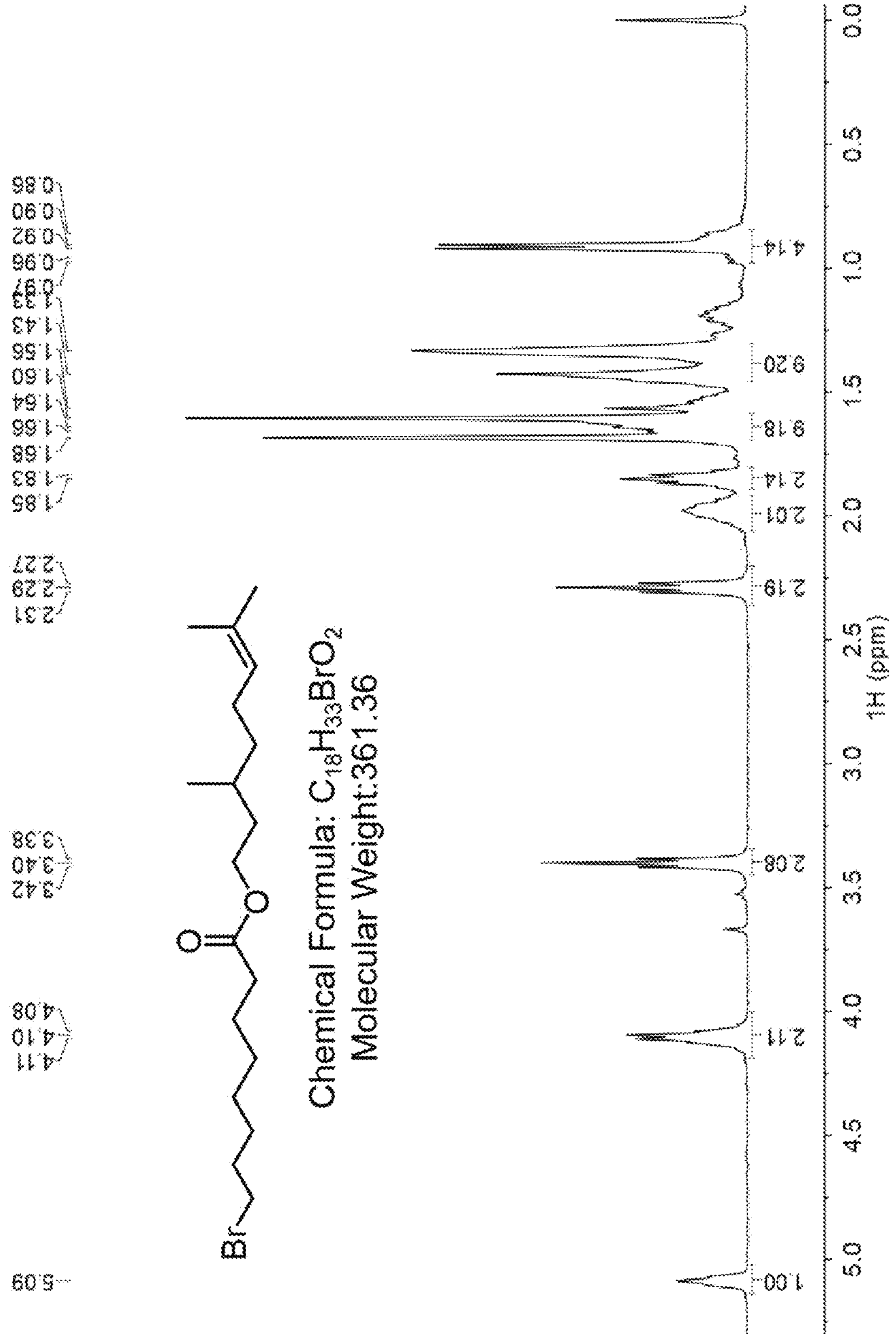
FIG. 3 shows a hydrogen spectrum of Compound 1-1.

Step 1: Synthesis of Compound 1-1:

8-bromooctanoic acid (1.139 g, 5.13 mmol) and citronellol (1.599 g, 10.25 mmol) were dissolved in dichloromethane (60 mL), after fully dissolved, EDC hydrochloride (0.98 g, 5.13 mmol) and DMAP (0.125 g, 1.03 mmol) were added. The mixture was stirred at room temperature for 18 hours. After the reaction was complete, the system was diluted with DCM (200 mL) and washed with saturated $NaHCO_3$ (100 mL) and saline (100 mL). The organic layers were merged and dried with anhydrous $Na_2SO_4$, the solvent was removed under vacuum to give a crude product, which was purified through chromatography (silica gel column, with an eluent being petroleum ether containing 0.5% EA (percent by volume)), and the purified product was evaporated to remove the eluent, to give a light yellow oily compound (0.648 g, 35%), the hydrogen spectrum of Compound 1-1 is shown in FIG. 3.

1H NMR (400 MHz, $CDCl_3$) δ: 5.09 (s, 1H), 4.18-4.01 (m, 2H), 3.40 (t, J=6.8 Hz, 2H), 2.29 (t, J=7.4 Hz, 2H), 1.98 (s, 2H), 1.84 (dd, J=14.3, 7.0 Hz, 2H), 1.70-1.60 (m, 9H), 1.38 (d, J=37.7 Hz, 9H), 0.89 (t, J=12.9 Hz, 4H).

Figure 6:
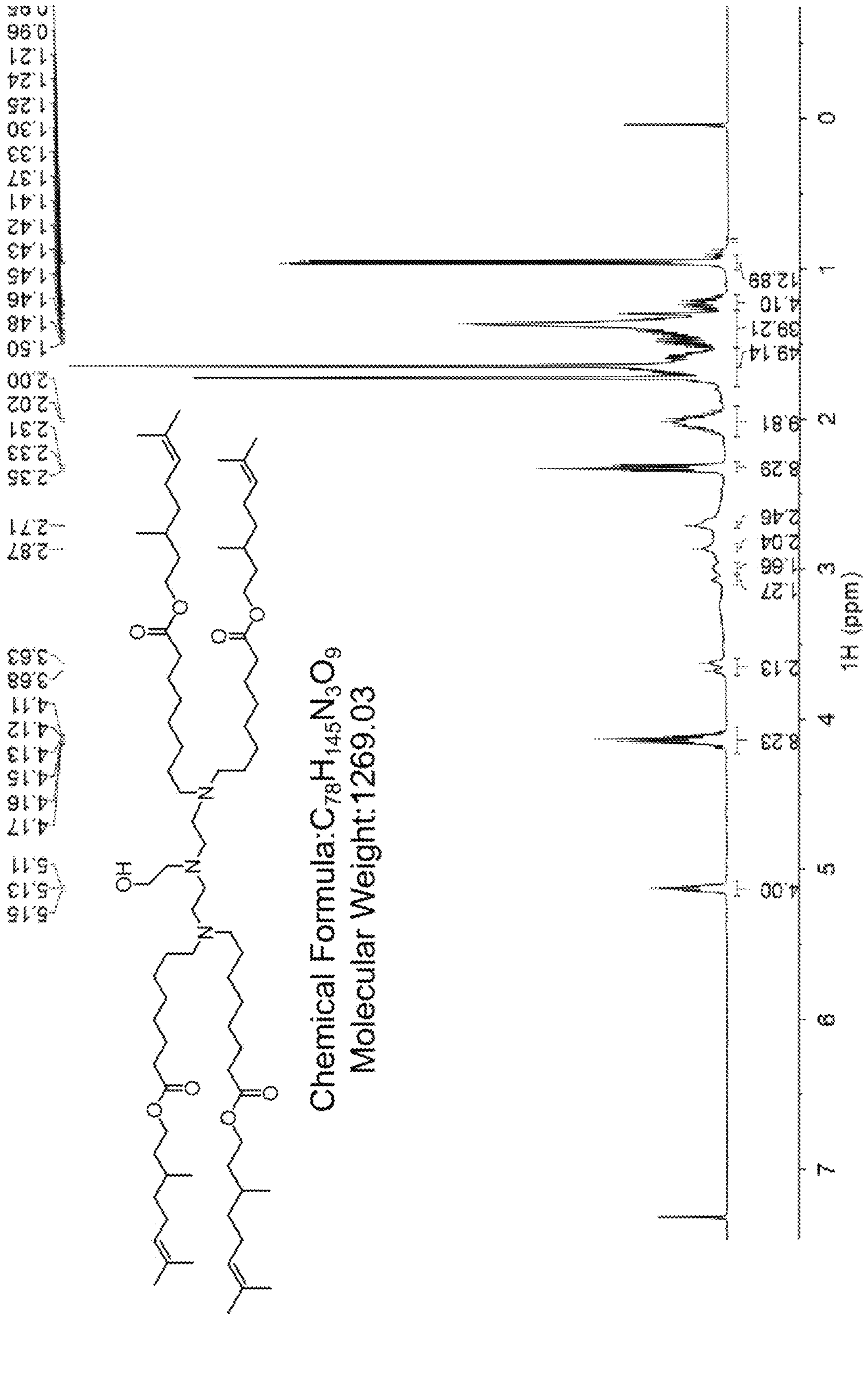
FIG. 6 shows a hydrogen spectrum of Compound 1.
Figure 7:
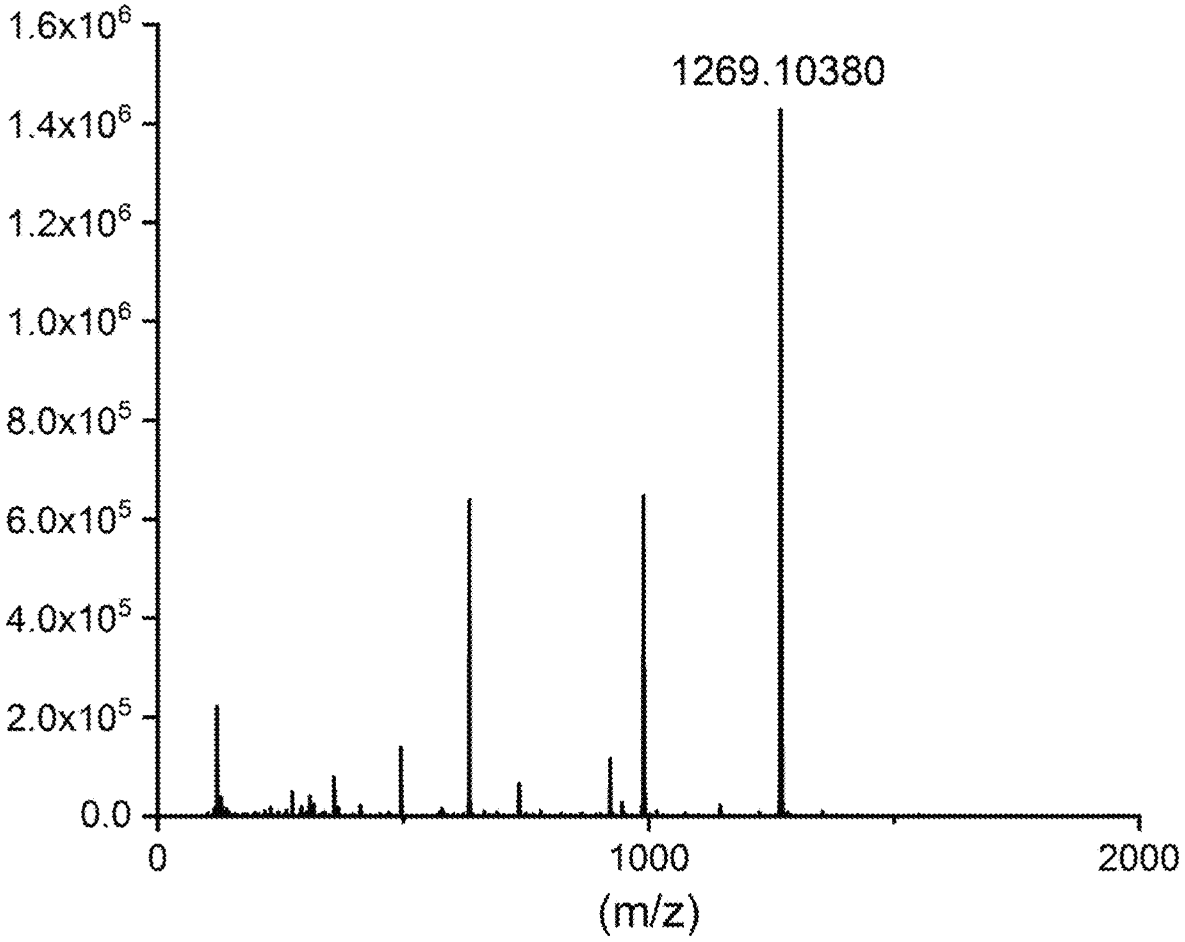
FIG. 7 shows a high-resolution mass spectrum of Compound 1.

Step 2: Synthesis of Compound 1:

2-(bis(2-aminoethyl) amino) ethyl-1-ol) (Compound a, 0.044 g, 0.30 mmol, its hydrogen spectrum is shown in FIG. 1) and 3,7-dimethyloct-6-enyl 6-bromohexanoic acid (0.398 g, 1.2 mmol) were added to a reaction flask and dissolved in THF/$CH_3CN$ (1:1, 6 mL), then DIPEA (0.155 g, 1.20 mmol) was added. The reactants were stirred at 63 °C for 72 h, cooled to room temperature, and the solvent was removed under vacuum. The crude product was extracted with ethyl acetate and saturated $NaHCO_3$, the organic layers were merged and dried with anhydrous $Na_2SO_4$, the solvent was removed under vacuum to give a crude product, which was purified through chromatography (silica gel column, with an eluent being dichloromethane containing 2% methanol (percent by volume)), and the purified product was evaporated to remove the eluent, to give a yellow oily Compound 1 (25.7 mg, yield 3.6%). The hydrogen spectrum of Compound 1 is shown in FIG. 6, and the mass spectrum is shown in FIG. 7.

1H NMR (400 MHz, $CDCl_3$) δ: 5.09 (s, 4H), 4.10 (dd, J=12.6, 6.5 Hz, 8H), 3.61 (d, J=21.6 Hz, 2H), 3.19 (s, 1H), 3.03 (s, 1H), 2.98-2.92 (m, 1H), 2.82 (s, 4H), 2.67 (s, 4H), 2.28 (t, J=7.5 Hz, 8H), 2.03-1.93 (m, 8H), 1.74-1.50 (m, 49H), 1.36 (ddd, J=44.4, 23.9, 10.0 Hz, 39H), 1.23-1.13 (m, 4H), 0.91 (d, J=6.5 Hz, 12H).

Example 2

The synthesis route of Compound 2

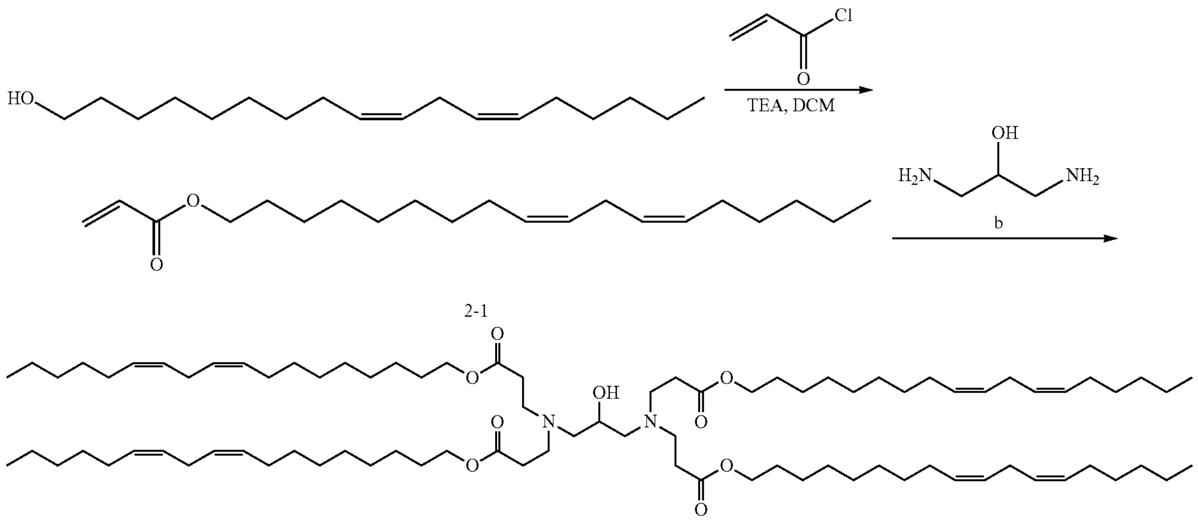

2-1

2

Figure 4:
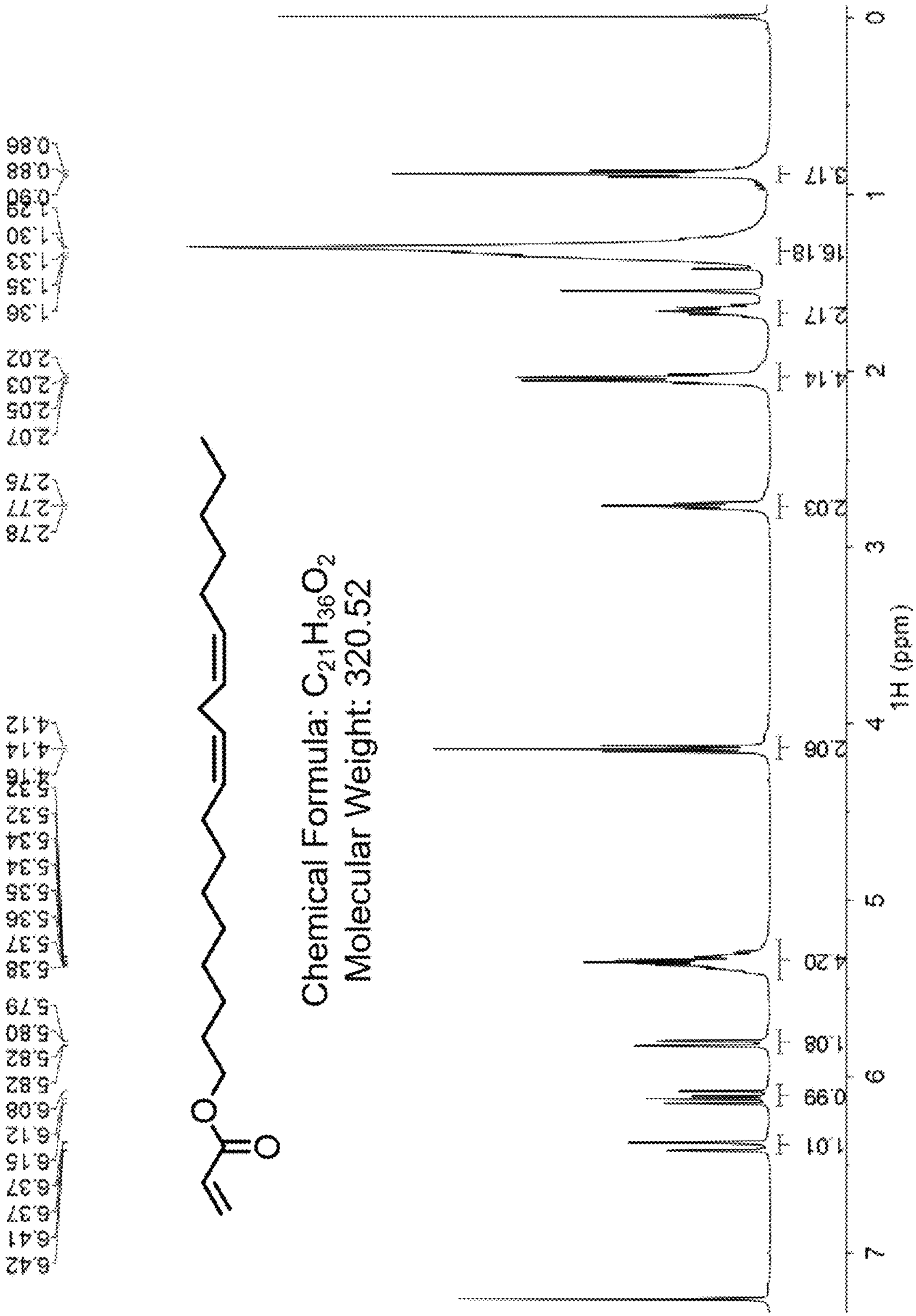
FIG. 4 shows a hydrogen spectrum of Compound 2-1.

Step 1: Synthesis of Compound 2-1:

Linolenic alcohol (0.267 g, 1 mmol) and triethylamine (0.133 g, 1.3 mmol) were added to a reaction flask in an ice water bath, dichloromethane (6 mL) was added. And acryloyl chloride (0.11 g, 1.2 mmol) was dissolved in dichloromethane (2.2 mL), and the mixture was added dropwise to the reaction flask slowly, and the reaction lasted for 10 minutes, the reaction was maintained below 10 °C, and finally, the ice bath was removed and the reaction solution was reacted at room temperature for 2 hours. The system was washed with saturated salt water to give a crude product, which was purified through chromatography (silica gel column, with an eluent being petroleum ether containing 0.5% EA (percent by volume)), and the purified product was evaporated to remove the eluent, to give a light yellow oily Compound 2-1 (0.173 g, yield 50%), the hydrogen spectrum of Compound 2-1 is shown in FIG. 4.

1H NMR (400 MHz, $CDCl_3$) δ: 6.41 (dd, J=17.3, 1.5 Hz, 1H), 6.13 (dd, J=17.3, 10.4 Hz, 1H), 5.82 (dd, J=10.4, 1.5 Hz, 1H), 5.47-5.26 (m, 4H), 4.16 (t, J=6.7 Hz, 2H), 2.78 (t, J=6.5 Hz, 2H), 2.06 (dd, J=13.6, 6.7 Hz, 4H), 1.75-1.60 (m, 2H), 1.39-1.17 (m, 16H), 0.88 (dt, J=10.4, 5.3 Hz, 3H).

Figure 2:
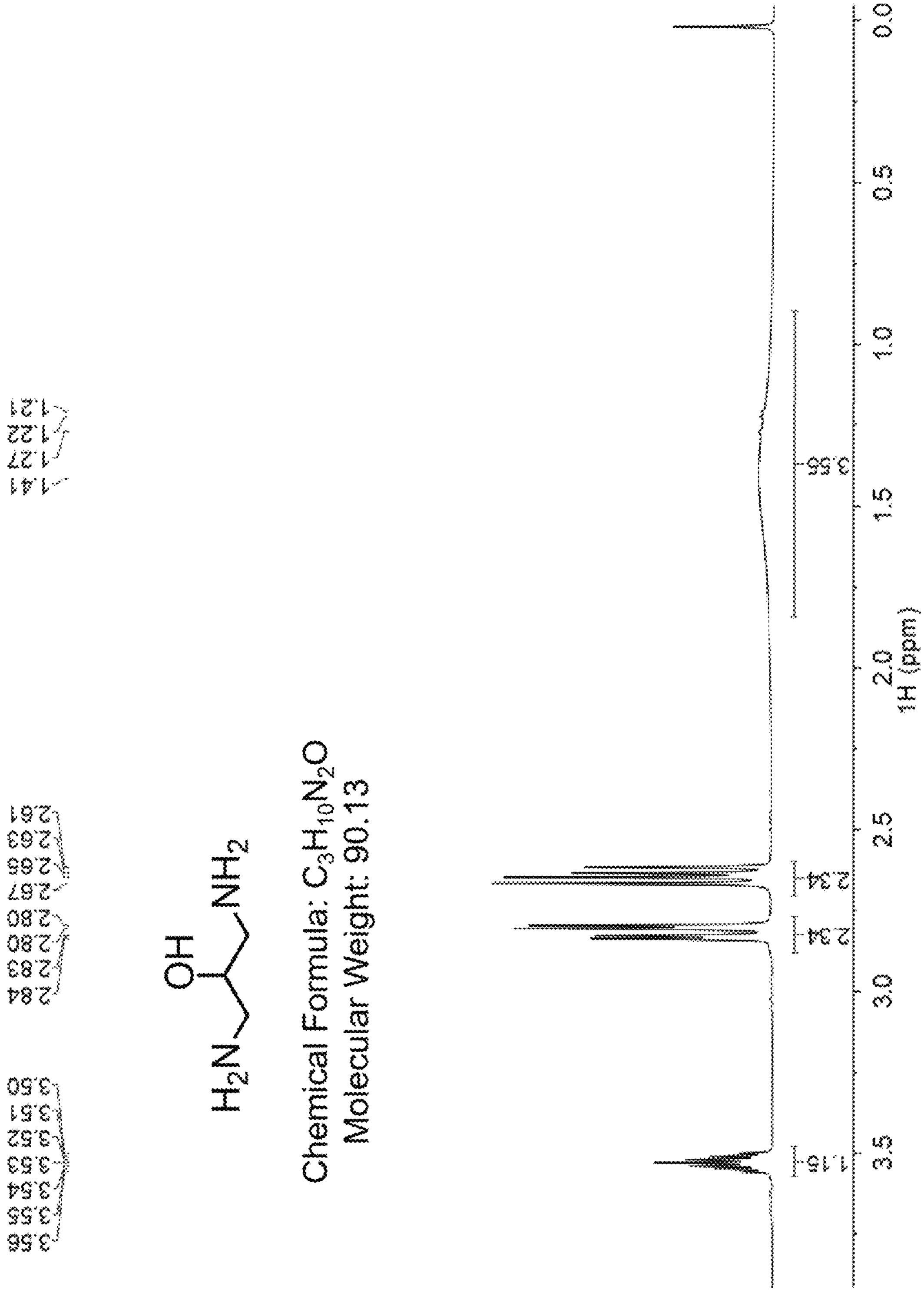
FIG. 2 shows a hydrogen spectrum of Compound b.
Figure 8:
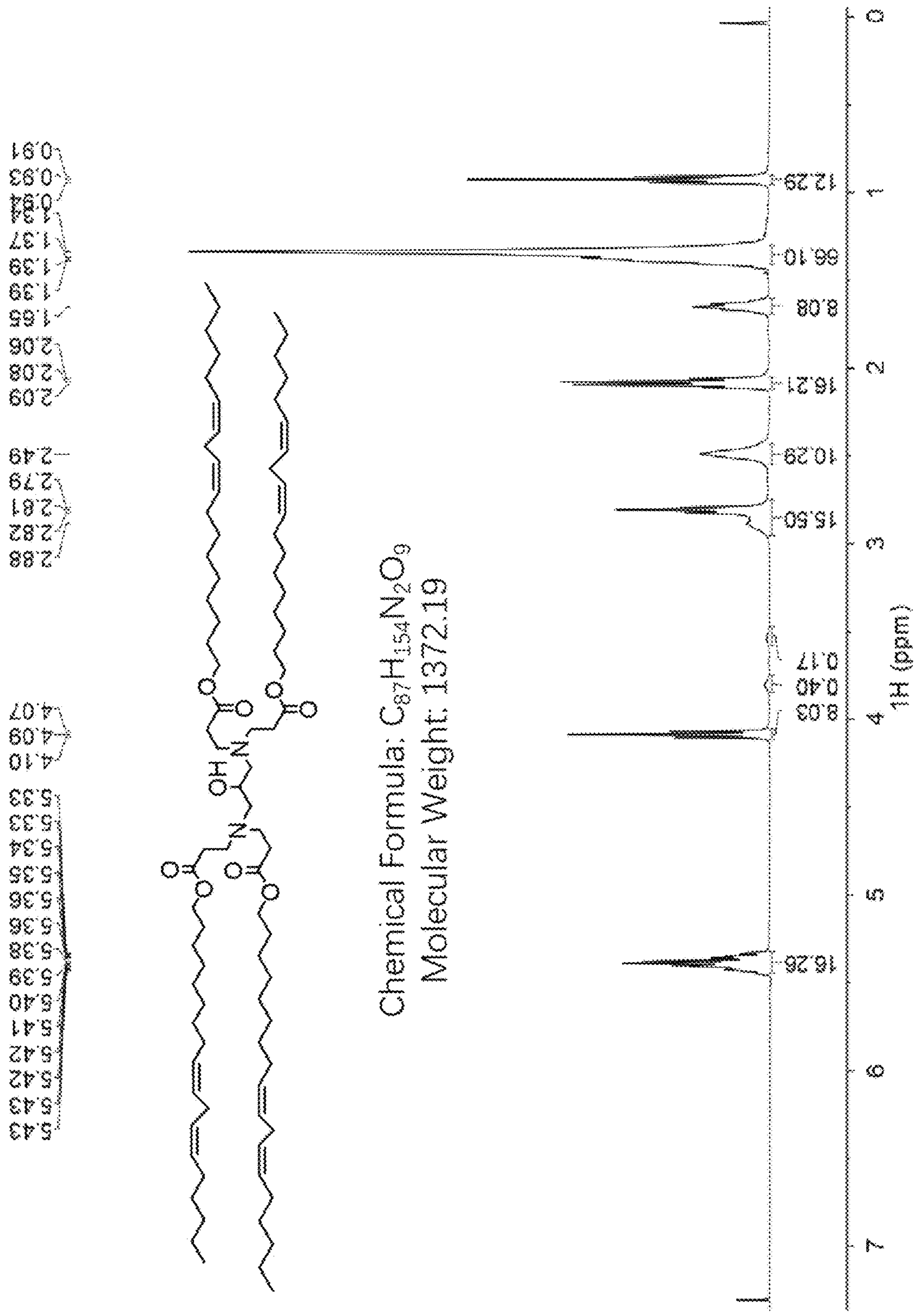
FIG. 8 shows a hydrogen spectrum of Compound 2.
Figure 9:
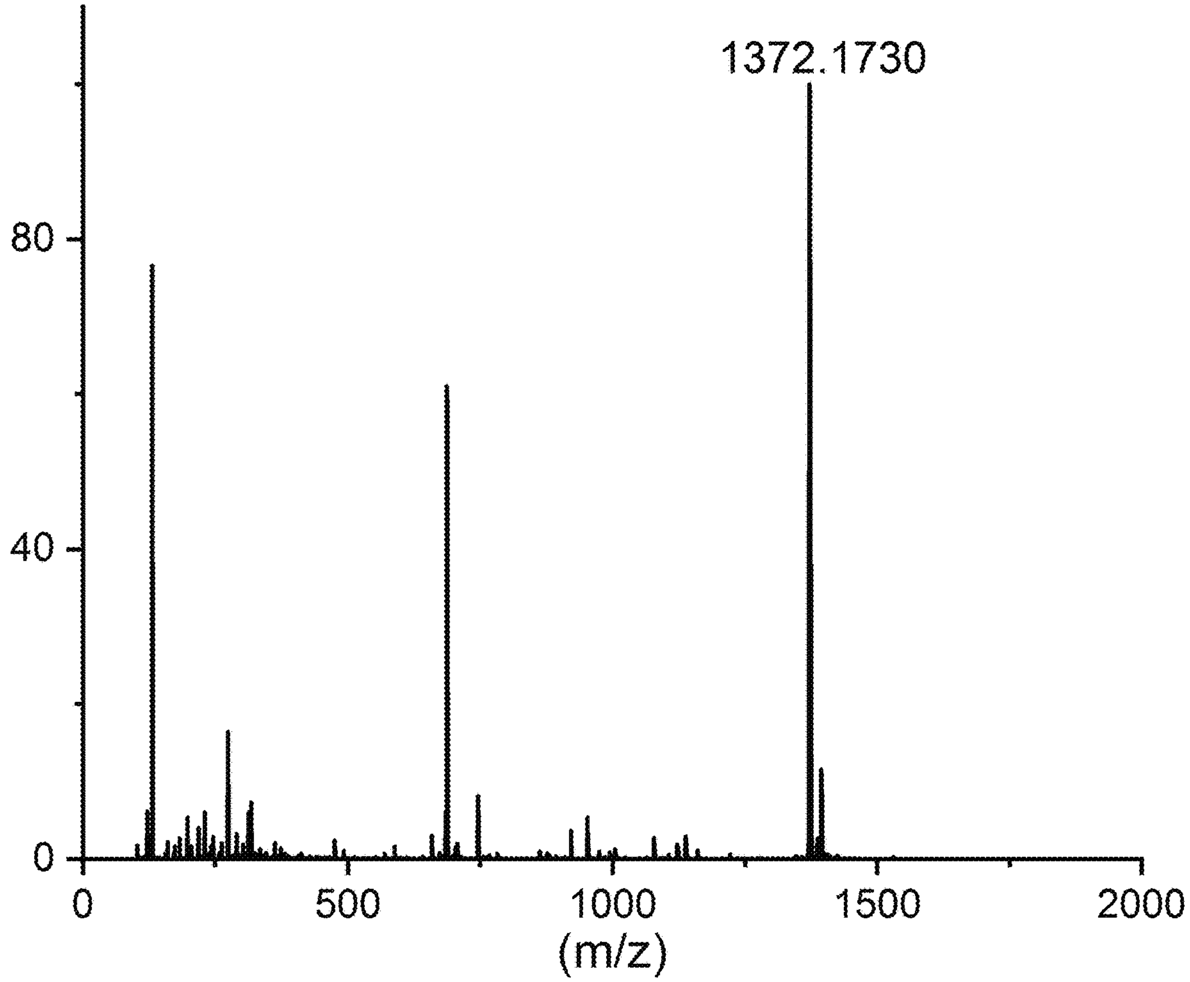
FIG. 9 shows a high-resolution mass spectrum of Compound 2.

Step 2: Synthesis of Compound 2:

1,3-diamino-2-propanol (Compound b, 0.04504 g, 0.50 mmol, its hydrogen spectrum is shown in FIG. 2) and 2-allylic acid (9z,12z)-octadecadienyl ester (0.64 g, 2 mmol) were added to a reaction flask and dissolved in THF/$CH_3CN$ (1:1, 6 mL), then DIPEA (0.155 g, 1.20 mmol) was added, and the system was reacted at 80 °C for 48 hours. The reaction system was cooled to room temperature, the solvent was removed under vacuum to give a crude product, which was purified through chromatography (silica gel column, with an eluent being dichloromethane containing 0.3% methanol (percent by volume)), and the purified product was evaporated to remove the eluent, to give a light yellow oily Compound 2 (20.58 mg, yield 3%). The hydrogen spectrum of Compound 2 is shown in FIG. 8, and the mass spectrum is shown in FIG. 9.

1H NMR (400 MHz, $CDCl_3$) δ 5.45-5.32 (m, 16H), 4.09 (t, J=6.8 Hz, 8H), 3.78 (d, J=20.7 Hz, 1H), 3.51 (d, J=27.2 Hz, 1H), 2.81 (t, J=6.4 Hz, 16H), 2.49 (s, 10H), 2.09 (q, J=6.8 Hz, 16H), 1.69-1.60 (m, 8H), 1.41-1.30 (m, 66H), 0.93 (t, J=6.8 Hz, 12H).

Example 3

The synthesis route of Compound 3

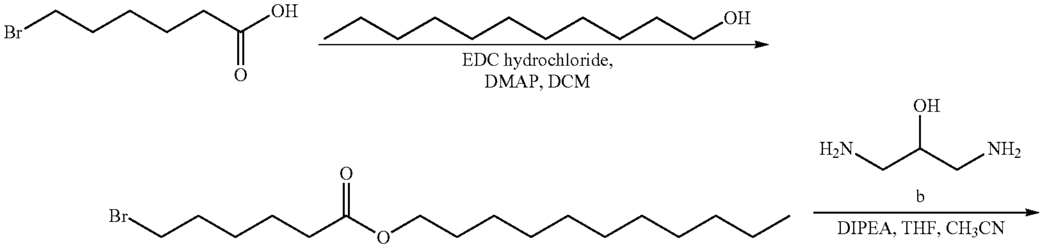

3-1

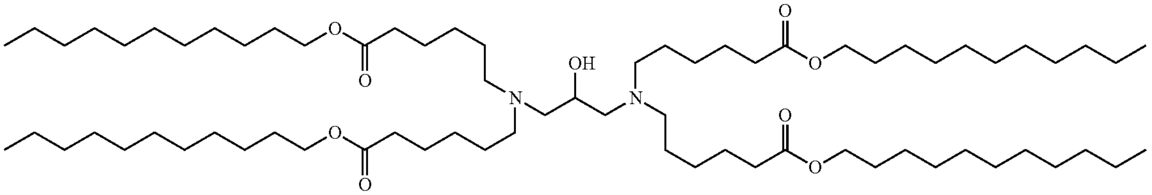

3

Figure 5:
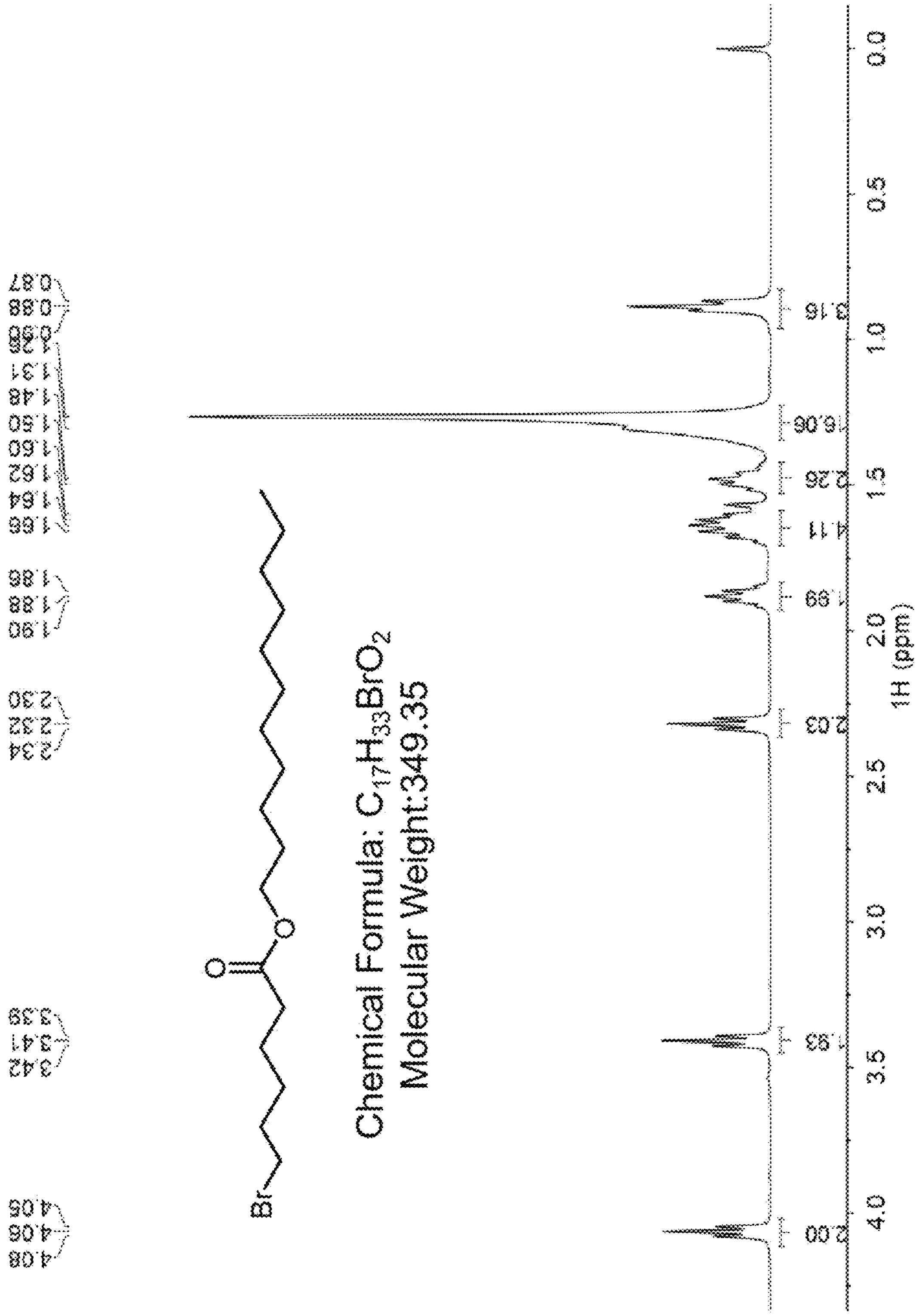
FIG. 5 shows a hydrogen spectrum of Compound 3-1.

Step 1: Synthesis of Compound 3-1:

6-bromohexanoic acid (1.0 g, 5.13 mmol) and undecanol (1.77 g, 10.25 mmol) were dissolved in dichloromethane (60 mL), then EDC hydrochloride (0.98 g, 5.13 mmol) and DMAP (0.125 g, 1.03 mmol) were added. The mixture was stirred at room temperature for 18 hours. After the reaction was complete, the system was diluted with DCM (200 mL) and washed with saturated $NaHCO_3$ (100 mL) and saline (100 mL). The organic layers were merged and dried with anhydrous $Na_2SO_4$, the solvent was removed under vacuum to give a crude product, which was purified through chromatography (silica gel column, with an eluent being petroleum ether containing 0.5% EA (percent by volume)), and the purified product was evaporated to remove the eluent, to give a light yellow oily Compound 3-1 (0.69 g, yield 38.6%). The hydrogen spectrum of Compound 3-1 is shown in FIG. 5.

1H NMR (400 MHz, $CDCl_3$) δ: 4.10 (t, J=6.6 Hz, 2H), 3.45 (t, J=6.7 Hz, 2H), 2.36 (t, J=7.3 Hz, 2H), 1.97-1.88 (m, 2H), 1.68 (tt, J=14.5, 7.3 Hz, 4H), 1.53 (dd, J=15.1, 7.9 Hz, 2H), 1.33 (d, J=16.9 Hz, 16H), 0.92 (t, J=6.5 Hz, 3H).

Figure 10:
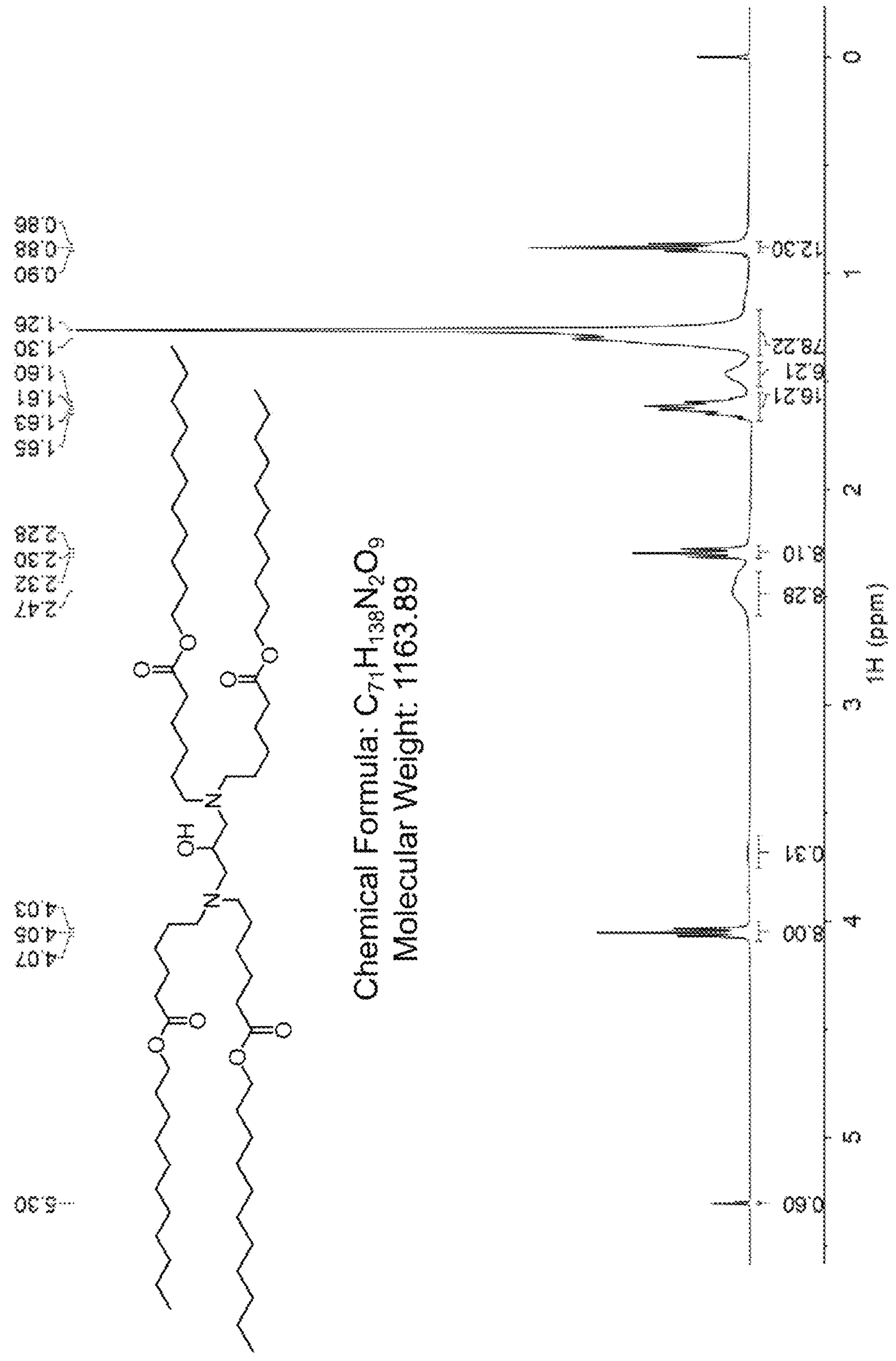
FIG. 10 shows a hydrogen spectrum of Compound 3.
Figure 11:
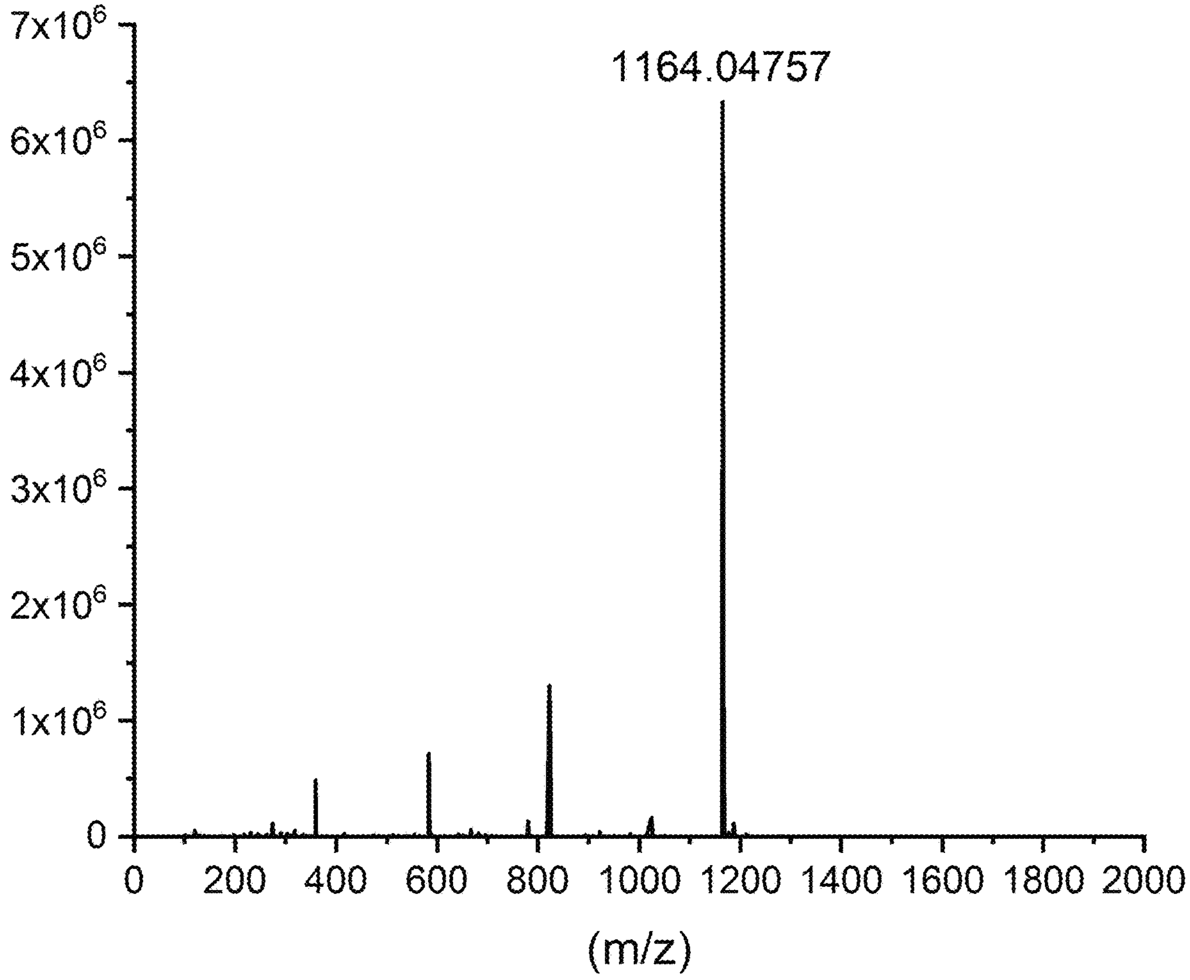
FIG. 11 shows a high-resolution mass spectrum of Compound 3.

Step 2: Synthesis of Compound 3:

1,3-diamino-2-propanol (0.027 g, 0.30 mmol) and undecyl 6-bromohexanoate (0.417 g, 1.20 mmol) were dissolved in THF/$CH_3CN$ (1:1, 6 mL), then DIPEA (0.155 g, 1.20 mmol) was added. The reactants were stirred at 63 °C for 72 h, cooled to room temperature, and the solvent was removed under vacuum. The crude product was extracted with ethyl acetate and saturated $NaHCO_3$, the organic layers were merged and dried with anhydrous $Na_2SO_4$, the solvent was removed under vacuum to give a crude product, which was purified through chromatography (silica gel column, with an eluent being dichloromethane containing 1% methanol (percent by volume)), and the purified product was evaporated to remove the eluent, to give a light yellow oily Compound 3 (47.72 mg, yield 4.1%). The hydrogen spectrum of Compound 3 is shown in FIG. 10, and the mass spectrum is shown in FIG. 11.

1H NMR (400 MHz, $CDCl_3$) δ 5.30 (s, 1H), 4.05 (t, J=6.8 Hz, 8H), 3.68 (s, 1H), 2.47 (s, 8H), 2.30 (t, J=7.5 Hz, 8H), 1.62 (dd, J=15.1, 7.7 Hz, 16H), 1.47 (s, 6H), 1.28 (d, J=16.8 Hz, 78H), 0.88 (t, J=6.8 Hz, 12H).

Example 4

Lipid Nanoparticles were Prepared and their Particle Size and Potential were Tested.

Preparation Method of Lipid Nanoparticles:

(1) According to the ionizable lipid compound: DSPC: DMG-PEG2000:cholesterol was 50:10:1.5:38.5 (in molar ratio), and anhydrous ethanol was used as the solvent, a lipid solution was prepared, the total concentration of each component was controlled to 50 mM, and after being dissolved and mixed well, and the solution was stored at −20 °C for later use.

(2) 25 mM sodium acetate buffer with a pH of about 5.2 was used to dissolve mRNA, and a nucleic acid preparation with a final concentration of approximately 0.1 mg/mL was prepared.

(3) Under the condition of a two-phase volume ratio of approximately 4:1 and a total rate of 12 mL/min, the lipid solution and nucleic acid preparation were mixed by hand vortex to form a lipid nanoparticle solution, the solution was immediately diluted by 20 times the volume using PBS buffer with pH 7.2 or sodium acetate buffer with pH 7.4, and then concentrated using a 10 KD ultrafiltration tube, the rotation speed of the centrifuge should not exceed the maximum speed limit of the ultrafiltration tube, after 2-3 times of fluid change, the solution environment of the lipid nanoparticles changed from pH 5.2 to 7.2, the lipid nanoparticle solution was finally concentrated to a final concentration of about 200 mM and stored at 4 °C for later use.

After the lipid nanoparticle solution was diluted by 50 times with 1×PBS, the particle size and PDI of the lipid nanoparticles were measured using Zetasizer Nano ZS (Malvern, Worcestershire, UK).

The lipid nanoparticles were diluted into 15 mM with PBS to measure the Zeta potential.

The Quant It RiboGreenRNA quantitative detection kit was used to determine the encapsulation rate on a Modular microporous multifunctional detector.

Figure 12:
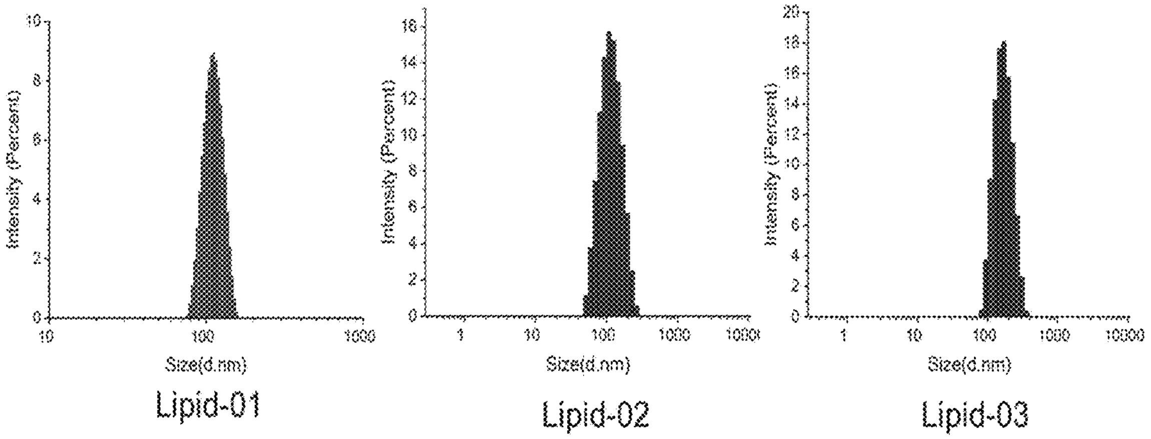
FIG. 12 is a particle size distribution diagram of lipid nanoparticles prepared in Example 4.

The testing results of particle size, PDI, encapsulation rate, and potential are shown in Table 1 and FIG. 12.

TABLE 1

| Lipid nanoparticles (LNP preparation) | Particle size (nm) | PDI (polydispersity index) | Encapsulation rate | Potential (mV) |
|---|---|---|---|---|
| Containing Compound 1 (Lipid-01) | 121 ± 5 | 0.12 | 92% | −15.6 |
| Containing Compound 2 (Lipid-02) | 131 ± 5 | 0.112 | 85% | −9.8 |
| Containing Compound 3 (Lipid-03) | 152 ± 5 | 0.136 | 90% | −20.2 |

Example 5: Animal In Vivo Transfection Experiment of Lipid Nanoparticles mRNA expressing Luciferase fluorescent protein was used, lipid nanoparticles were prepared according to the preparation method of Example 4, wherein the amount of mRNA used was 120 μg, and the total amount of the ionizable lipid compound, DSPC, DMG-PEG2000, and cholesterol was 1200 μg, and the lipid environment was rapidly converted using 400 μL of neutral PBS buffer.

The prepared lipid nanoparticles were quickly injected into the medial muscles of the hind limbs of 6-8-week-old female Babl/c mice via intramuscular injection (IM), with 30 g of mRNA injected into the left and right hind limbs, respectively. At different time periods after injection, the expression of luciferase in mice was observed using a Small Animal Imaging Instrument.

The prepared lipid nanoparticles were quickly injected through the tail vein to 6-8-week-old female Babl/c mice (IV), with a mRNA injection amount of 60 g. At different time periods after injection, the expression of luciferase in the mice was observed using a small animal imager.

After 4 hours, fluorescence imaging was performed on the heart, liver, spleen, lungs, and kidneys of the mice.

Figure 13:
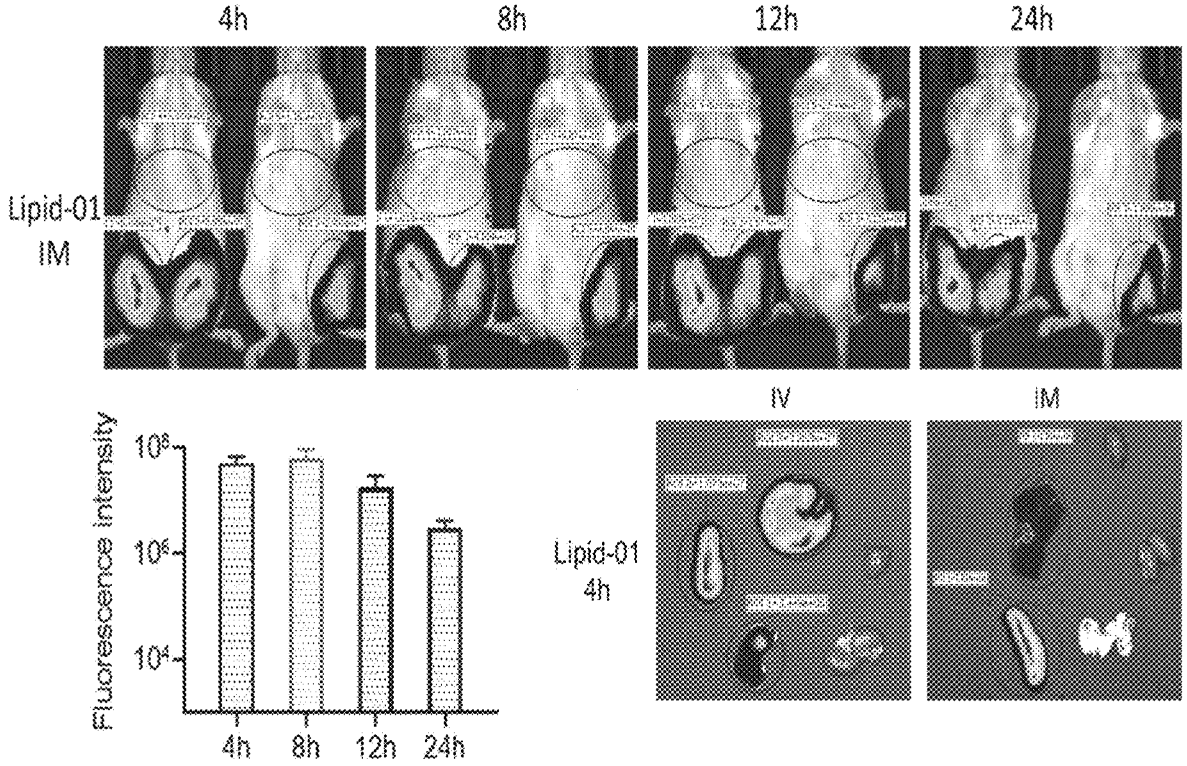
FIG. 13 shows the in vivo delivery effect of Lipid-01 lipid nanoparticles in mice in Example 5.

The delivery effect of Lipid-01 lipid nanoparticles in mice is shown in FIG. 13, and the results show that the fluorescence expression can reach $7\times10^7$ after 4 hours of intramuscular injection, and imaging of various organs in mice shows that the fluorescence expression in the organs after intramuscular injection is mainly concentrated in the spleen (80%), the fluorescence expression after intravenous injection is distributed in the liver (63%), spleen (31%), and lungs (6%), indicating that the intramuscular injection of Lipid-01 has good spleen targeting.

Figure 14:
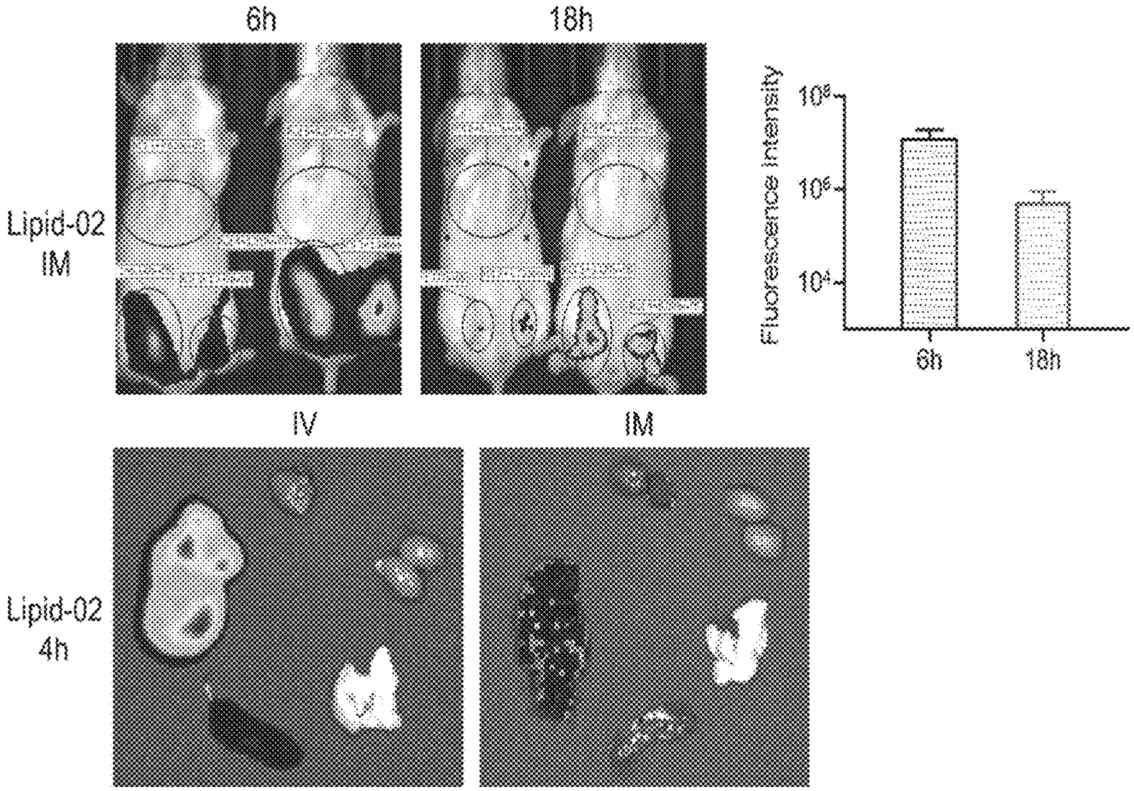
FIG. 14 shows the in vivo delivery effect of Lipid-02 lipid nanoparticles in mice in Example 5.

The delivery effect of Lipid-02 lipid nanoparticles in mice is shown in FIG. 14, and the results show that the fluorescence expression is about $10^7$ after 6 hours of intramuscular injection, and through imaging of various organs in mice, it can be seen that the fluorescence expression in the organs after intravenous injection is mainly distributed in the liver, while the fluorescence expression in the liver of mice after intramuscular injection is lower, indicating that Lipid-02 is more suitable for intramuscular injection.

Figure 15:
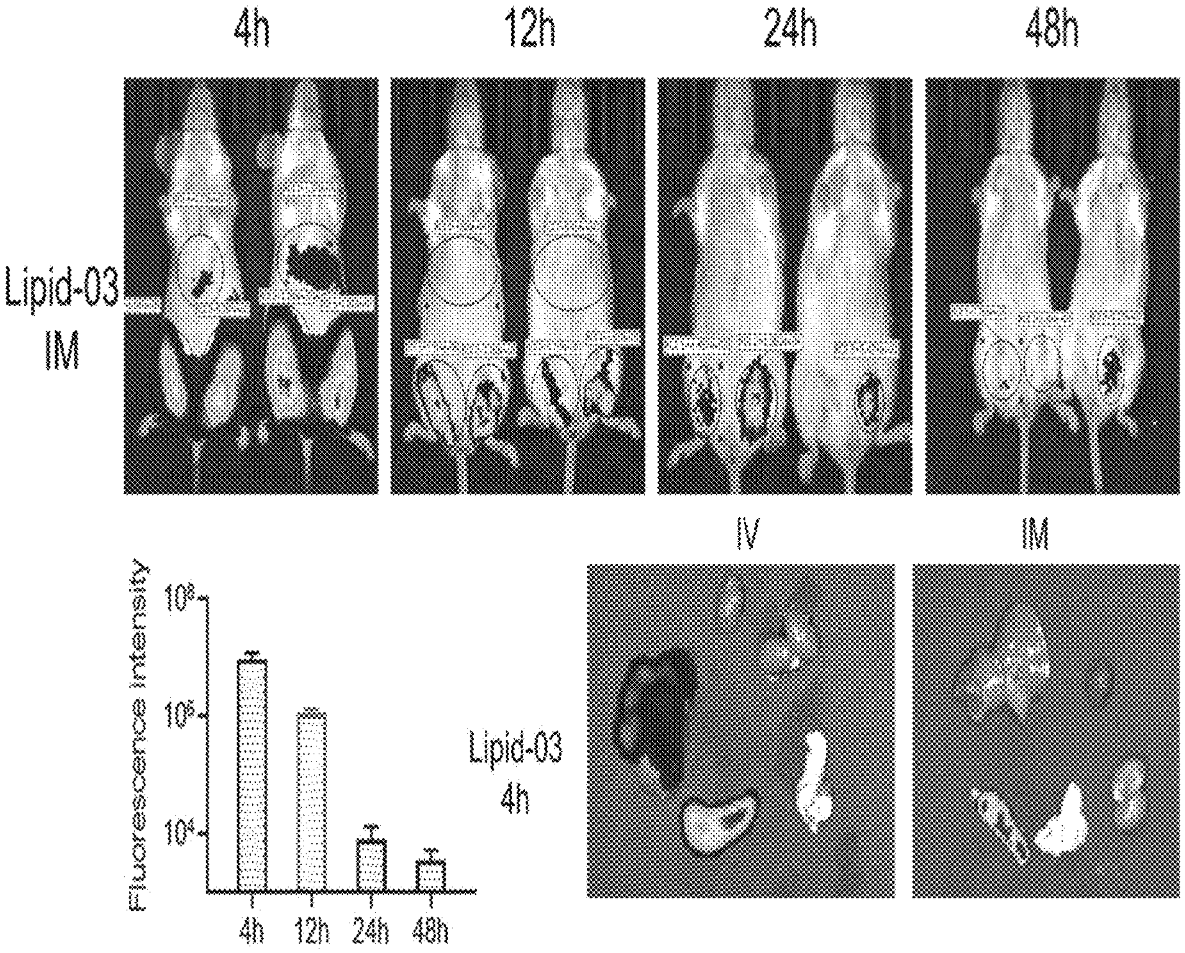
FIG. 15 shows the in vivo delivery effect of Lipid-03 lipid nanoparticles in mice in Example 5.

The delivery effect of Lipid-03 lipid nanoparticles in mice is shown in FIG. 15, and the results show that the fluorescence expression is about $10^7$ after 4 hours of intramuscular injection, and through imaging of various organs in mice, it can be seen that the fluorescence in the organs after intramuscular and intravenous injection is concentrated in the spleen, indicating that Lipid-03 has good spleen targeting by intramuscular and intravenous injection.

The above detailed describes the present disclosure, is intended to make those PA with the technology in the art being able to understand the content of the present disclosure and thereby implement it, and should not limit the protective scope of this disclosure. Any equivalent variations or modifications according to the spirit of the present disclosure should be covered by the protective scope of the present disclosure.

The invention claimed is:

1. An ionizable lipid compound shown in general formula (I) or general formula (II),

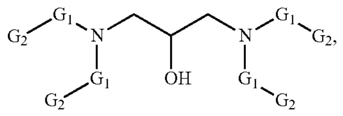

(I)

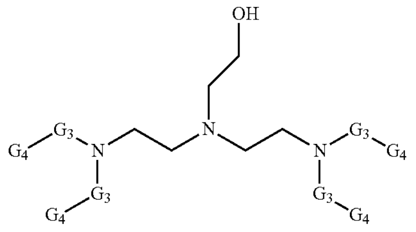

(II)

wherein, in general formula (I), $G_1$ is $C_1$-$C_{10}$ linear alkylidene, $G_2$ is —OC(═O)R, —C(═O)OR or —C(═O)NHR, R is $C_5$-$C_{20}$ linear alkyl or

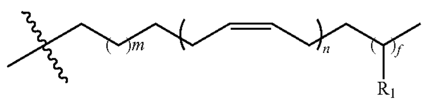

or

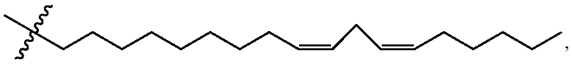

, or $R_1$ is hydrogen, methyl, ethyl, or isopropyl, m is an integer between 1-10, n is an integer between 1-5, and f is an integer between 1-5;

in general formula (II), $G_3$ is $C_1$-$C_{10}$ linear alkylidene, $G_4$ is —OC(═O)R', —C(═O)OR' or —C(═O)NHR', R' is

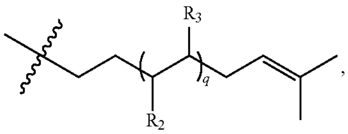, $R_2$ and $R_3$ are independently hydrogen, methyl, ethyl, or isopropyl, q is an integer between 1-3.

2. The ionizable lipid compound according to claim 1, wherein $G_1$ is $C_2$-$C_8$ linear alkylidene;

and/or, $G_3$ is $C_5$-$C_{10}$ linear alkylidene;

and/or, $R_1$ is hydrogen;

and/or, m is an integer between 3-8;

and/or, f is an integer between 1-4;

and/or, R is $C_5$-$C_{15}$ linear alkyl or

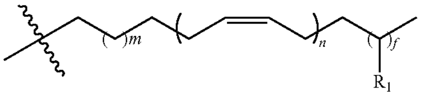

or

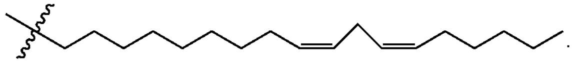.

3. The ionizable lipid compound according to claim 2, wherein m is an integer between 4~6 and/or f is 2 or 3.

4. The ionizable lipid compound according to claim 1, wherein $G_2$ is —C(=O)OR and/or, $G_4$ is —C(=O)OR';

and/or, $R_2$ is methyl, and $R_3$ is hydrogen.

5. The ionizable lipid compound according to claim 1, wherein the ionizable lipid compound is one or more of the following compounds:

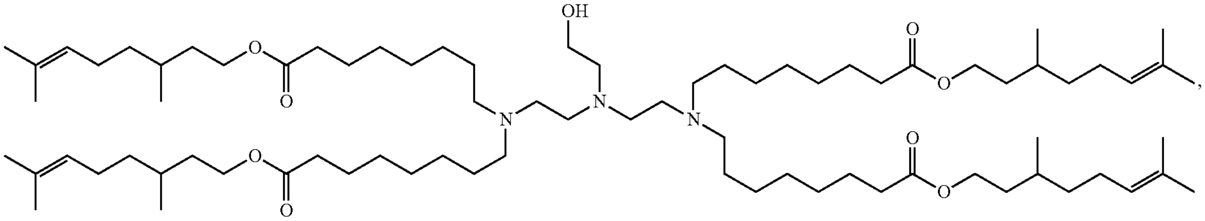,

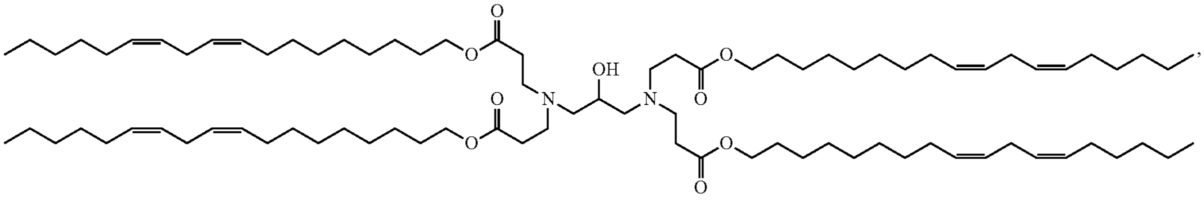,

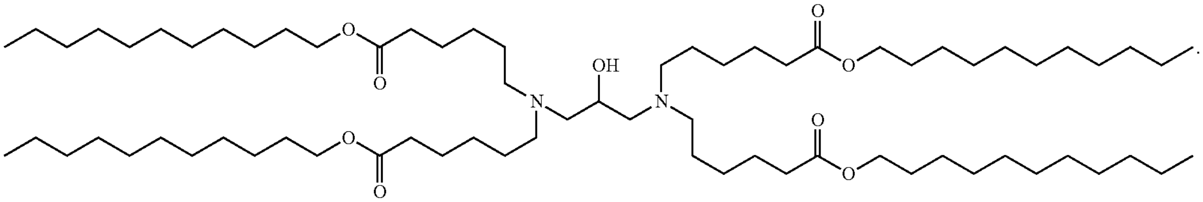.

6. A delivery carrier comprising one or more of ionizable lipid compounds shown in general formula (I) and general formula (II) of claim 1.

7. The delivery carrier according to claim 6, wherein the delivery carrier further comprises a helper molecule, and a feeding molar ratio of the ionizable lipid compound to the helper molecule is (0.1-1):(0.1-1).

8. The delivery carrier according to claim 7, wherein the helper molecule comprises one or more of synthetic or naturally sourced helper lipid or lipoid molecules, animal-sourced cells or vesicles, polypeptide molecules, polymer molecules, carbohydrate molecules or inorganic substances.

9. The delivery carrier according to claim 8, wherein the helper molecule comprises one or more of cholesterol, calcipotriol, stigmasterol, lupeol, β-sitosterol, betulin, ursolic acid, oleanolic acid, dioleoyl phosphatidylcholine, distearoyl phosphatidylcholine, 1-stearoyl-2-oleoyl phosphatidylcholine, dioleoyl phosphatidylethanolamine, (1,2-dioleyloxy-propyl) trimethylammonium chloride, dodecyl dimethyl ammonium bromide, 1,2-dimyristoyl-sn-glycero-3-ethyl phosphocholine, dipalmitoyl phosphatidylethanolamine-methoxy polyethylene glycol 5000, distearoyl phosphatidylethanolamine-polyethylene glycol 2000, activated carbon, silica and calcium phosphate.

10. The delivery carrier according to claim 7, wherein the ionizable lipid compound and/or the helper molecule is modified with a targeting substance, and the targeting substance comprises one or more of folic acid, single-chain antibodies and targeting polypeptides.

11. The delivery carrier according to claim 6, wherein the delivery carrier is a lipid nanoparticle, the lipid nanoparticle has a particle size of 50 nm-200 nm; and/or, the lipid nanoparticle has a polydispersity index of ≤0.4.

12. The delivery carrier according to claim 11, wherein the delivery carrier is able to deliver a nucleic acid molecule, and the nucleic acid molecule comprises one or more of plasmid DNA (pDNA), siRNA, ASO, and mRNA; and/or, a mass ratio of the nucleic acid molecule to the delivery carrier is 1:(5-50).

13. The delivery carrier according to claim 9, wherein the delivery carrier and a nucleic acid molecule constitute a nucleic acid drug composition, wherein the nucleic acid drug composition further comprises a pharmaceutical available additive, and the additive comprises one or more of an excipient, a stabilizer, and a diluent.

14. The delivery carrier according to claim 13, wherein an amount of the additive accounts for 1%-20% of a total mass of the drug composition.

15. The delivery carrier according to claim 6 wherein the delivery carrier or a nucleic acid drug composition is a freeze-dried powder or an injection, which is locally administered by microneedles, injection or perfusion through muscle, subcutaneous, endothelium or intra-tumor, or is administered by intravenous injection.

16. The delivery carrier according to claim 6, wherein the ionizable lipid compound is one or more of the following compounds:

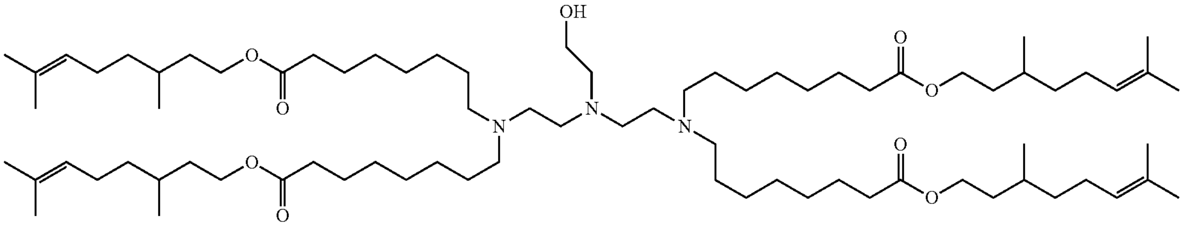
,
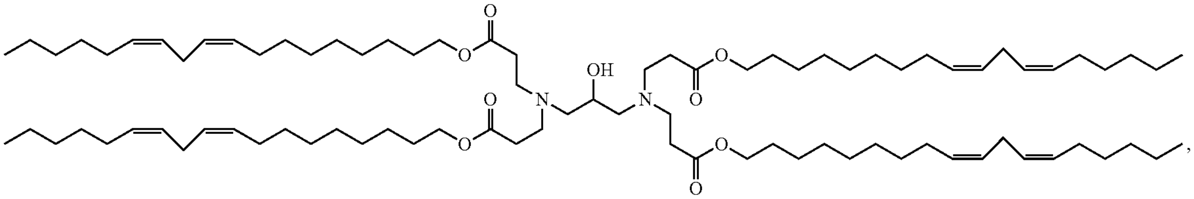
,
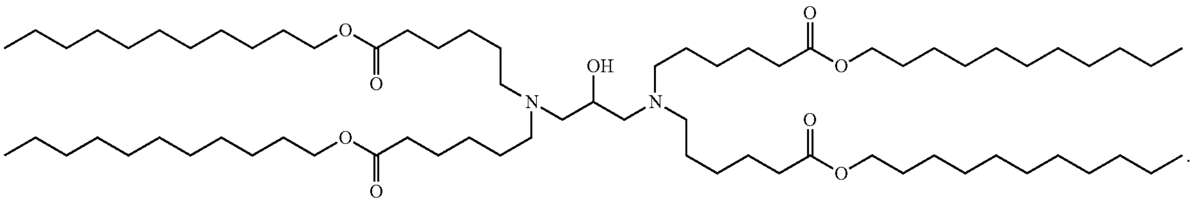
.

17. A method for in vivo delivery of nucleic acid molecules comprising administering the delivery carrier according to claim 6 to deliver the nucleic acid molecules to the body of a subject.

18. The method for in vivo delivery of nucleic acid molecules according to claim 17, wherein the subject is a mammal.

19. The method for in vivo delivery of nucleic acid molecules according to claim 17, wherein the subject is human.

20. The method for in vivo delivery of nucleic acid molecules according to claim 17, wherein the delivery carrier comprises one or more of the following ionizable lipid compounds:

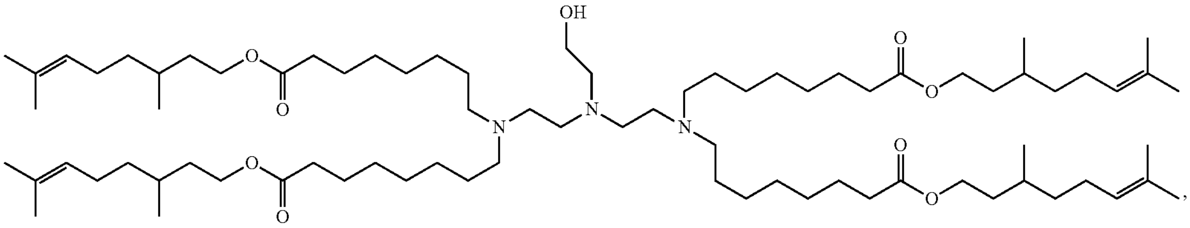
,

-continued
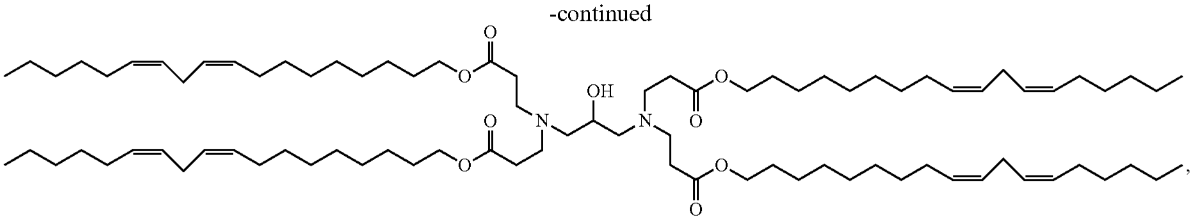
,
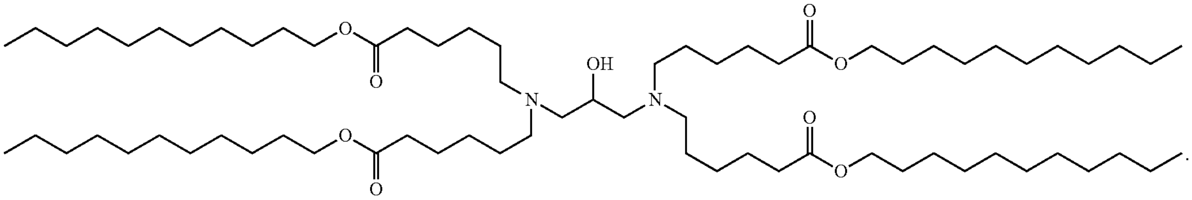
.
* * * * *